US012491119B2

(12) United States Patent
Bernet et al.

(10) Patent No.: US 12,491,119 B2
(45) Date of Patent: Dec. 9, 2025

(54) BANDAGE, IN PARTICULAR A COMPRESSION BANDAGE

(71) Applicant: IVF HARTMANN AG, Neuhausen am Rheinfall (CH)

(72) Inventors: Claudia Bernet, Marthalen (CH); Tobias Hoesl, Lauchringen (DE); Markus Rothmaier, Illnau (CH)

(73) Assignee: IVF HARTMANN AG, Neuhausem am Rheinfall (CH)

( * ) Notice: Subject to any disclaimer, the term of this patent is extended or adjusted under 35 U.S.C. 154(b) by 531 days.

(21) Appl. No.: 16/637,020

(22) PCT Filed: Jul. 26, 2018

(86) PCT No.: PCT/EP2018/070332
§ 371 (c)(1),
(2) Date: Feb. 6, 2020

(87) PCT Pub. No.: WO2019/030011
PCT Pub. Date: Feb. 14, 2019

(65) Prior Publication Data

US 2020/0253785 A1 Aug. 13, 2020

(30) Foreign Application Priority Data

Aug. 7, 2017 (DE) ..................... 10 2017 117 828.7

(51) Int. Cl.
*A61F 13/01* (2024.01)
*A61F 13/00* (2024.01)

(52) U.S. Cl.
CPC .. *A61F 13/01038* (2024.01); *A61F 13/01042* (2024.01); *A61F 2013/00119* (2013.01); *A61F 2013/0028* (2013.01)

(58) Field of Classification Search
CPC .......... A61F 13/00038; A61F 13/00043; A61F 13/00021; A61F 13/00029; A61F 13/0273;
(Continued)

(56) References Cited

U.S. PATENT DOCUMENTS 2,212,862 A * 8/1940 Hirsh ..................... A44B 11/04 24/336
3,156,242 A * 11/1964 Crowe, Jr. ............ B29C 66/433 156/72

(Continued)

FOREIGN PATENT DOCUMENTS

DE 2515786 A1 10/1976
WO 9729689 A1 8/1997
WO WO-2015188225 A1 * 12/2015 ....... A61F 13/00021

OTHER PUBLICATIONS

German Search Report of German Priority Application dated Mar. 22, 2018.

(Continued)

*Primary Examiner* — Caitlin A Carreiro
(74) *Attorney, Agent, or Firm* — LEYDIG, VOIT & MAYER, LTD.

(57) ABSTRACT

The invention relates to a bandage (10) comprising a flat material web (12) having a first (14) and a second (16) side and a first (18) and a second (20) end spaced apart in the longitudinal direction of the bandage (10), a wound pad (22) on the first side of the flat material web (12), a pressure application means (32) on the second side (16) of the flat material web (12) opposite the wound pad (22), a securing element (24) on the second end (20) of the flat material web (12) for securing the second end (20) of the flat material web (12) on or to itself for a bandage (10) positioned on a carrier.

26 Claims, 1 Drawing Sheet

(58) Field of Classification Search

Figure 1:
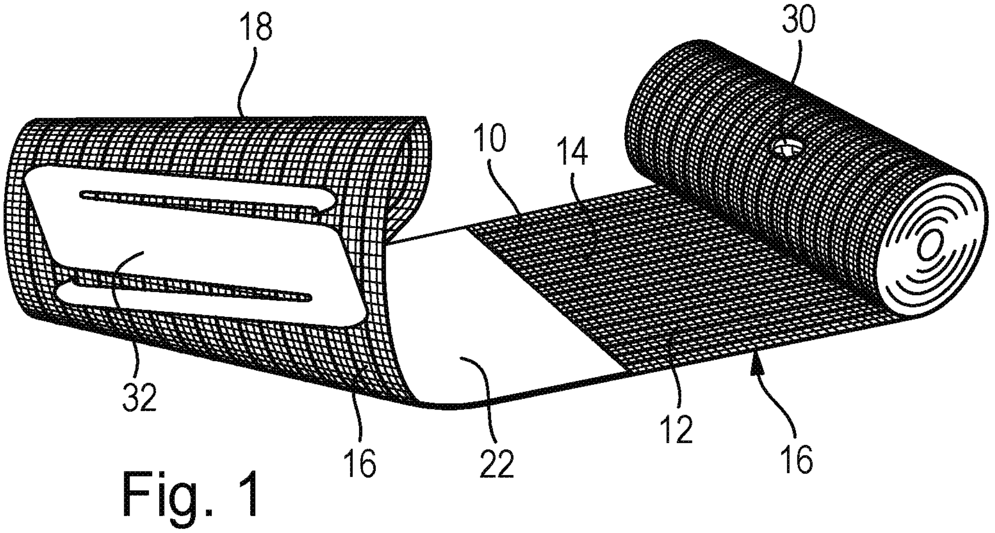

CPC .... A61F 2013/00119; A61F 2013/0028; A61F 2013/00106; A61F 2013/00102; A61F 2013/00174; A61F 2013/00468; A61F 2013/00731; A61F 2013/00463; A61F 2013/00089; A61F 13/00; A61F 5/30; A61B 17/132-1327; A61B 17/0487

USPC ........... 602/76, 41-42, 53, 75; 606/201, 203

See application file for complete search history.

(56) References Cited

U.S. PATENT DOCUMENTS

| | | | | |
|---|---|---|---|---|
| 4,005,709 | A | 2/1977 | Laerdal | |
| 4,377,159 | A * | 3/1983 | Hansen | A61F 13/0203 602/53 |
| 5,628,723 | A * | 5/1997 | Grau | A61B 17/1325 602/53 |
| 5,990,402 | A * | 11/1999 | Epstein | G10D 13/063 84/453 |
| 7,972,288 | B2 * | 7/2011 | Chabba | A61F 13/04 602/76 |
| 2003/0199801 | A1 * | 10/2003 | Harder | A61F 13/00 602/78 |
| 2007/0185428 | A1 | 8/2007 | Harder | |
| 2009/0208698 | A1 * | 8/2009 | Langen | A61F 13/622 428/100 |
| 2011/0313435 | A1 | 12/2011 | Aldrige et al. | |

OTHER PUBLICATIONS

First Chinese Office Action from Chinese Patent Application No. 201880065273.0 dated Apr. 21, 2021.

* cited by examiner

BANDAGE, IN PARTICULAR A COMPRESSION BANDAGE

This application claims priority to German Patent Application No. DE102017117828.7 filed on Aug. 7, 2017, the contents of which are incorporated by reference herein in their entirety.

The invention relates to a bandage, in particular a compression bandage, for the initial treatment of injuries. The prior art discloses multiple bandages and bindings, wherein the term “bandages” and “bindings” are to be used synonymously below, which are used for different purposes. In this case, bandages are known which are to be used for the initial treatment of injuries, this frequently being injuries and wounds caused by trauma which frequently involve heavy bleeding. For such purposes, which can also be described as emergency situations, it is known to use bandages which, on the one hand, comprise a wound dressing pad which is applied on one side of the flat material web from which the bandage as such consists, and on the other side a pressure applicator is provided which enables sufficient compression to be applied to the wound.

It is important precisely in the case of heavily bleeding wounds to apply sufficient pressure in order to avoid too much blood loss.

This thus disclosed in the prior art, is for example WO 97/29689 A1, which describes a binding with a sterile wound dressing pad, wherein on the rear side located opposite the wound dressing pad a pressure applicator is provided, through which the binding is threaded through and which then applies increased pressure on a wound located underneath it. A disadvantage in the design, in this case, is that the applied pressure is applied on a relatively small surface and the pressure distribution is inhomogeneous.

In addition, for example US 2003/199801 A1 discloses a design where a hook-shaped element is provided on the rear side of the binding. Once the first winding of the bandage has been applied and said bandage is fixed to a part of the body, on the next winding the bandage is then passed through the hook, and after this the direction of winding is changed. Tensile forces, which are introduced into the relevant area of the body via the center of the wound dressing pad, can be applied as a result and thereby a more uniform pressure is to be exerted. A disadvantage in this connection is that the binding can be displaced as a result of the one-sided tensile forces.

A further improvement is then shown in US 2007/0185428 A1. This shows an H-shaped element centrally above the wound dressing pad for applying pressure onto an injury. In this case, after a first fixing, the binding continues to be wound around the limb in order then to be looped around a side part of the H-shaped element and thus to carry out a directional change, as a result of which a first tension can be applied. When reaching the H-shaped element again, the bandage is then guided, in turn, around the second side part of the H in order to carry out another directional change. A more uniform application of tensile forces is then possible.

A disadvantage in the case of the present design is that as a result of the guiding around the H-shaped element, the contact area of the bandage is decreased in said region and the bandage needs a certain length until it is spread out over its full width again. Furthermore, the H-shaped element is comparatively small with regard to the surface so that the pressure applied as a result of the tensioning of the binding is rather low and not particularly flat.

The object of the invention is now to provide a bandage which is able to be applied to and can treat injuries in a simple manner, in particular even in emergency situations, simple manageability being particularly important in emergency situations.

The invention achieves said object by a bandage with the following features of claim 1, namely a bandage including a. a flat material web having a first and a second side and a first and second end which are spaced apart in the longitudinal direction of the bandage, b. a wound dressing pad on the first side of the flat material web, c. a pressure applicator on the second side of the flat material web opposite the wound dressing pad, d. a fastening element at the second end of the flat material web for fastening the second end of the flat material web on or to itself when the bandage is positioned on a carrier, wherein the pressure applicator comprises a base plate and two elongated fixing elements which are arranged in the longitudinal direction of the bandage on both sides of the base plate and extend at an angle, in particular perpendicular, to the longitudinal direction of the bandage, wherein in each case the one end of the fixing elements is secured to the base plate and the other end is free and the fixing elements realize a gap between them and the base plate over their remaining length.

As a result of providing two elongated fixing elements in the longitudinal direction on both sides of a base plate, when the bandage is placed in position, analogously to the prior art, the bandage is able to be guided through between the base plate and the fixing elements in order then to carry out a directional change with reference to the direction of winding around the body part and then to be wound around the body part further until the second fixing element is reached, wherein the bandage is then once again guided through between fixing element and base plate and once again there is a change in the direction of the positioning of the bandage so that pressure, which acts more uniformly in both directions (longitudinal direction of the bandage), is able to be applied to the injury through the base plate as a result of tightening the bandage.

The provision of elongated fixing elements is particularly advantageous in this case as wrapping the bandage around the pressure applicator does not result in the bandage width being constricted. In fact, the pressure, applied via tightening, onto the base plate can be produced in a very uniform manner onto an injury over the entire width of the bandage. In this case, the pressure applicator comprises a substantially W-shaped or S-shaped form, consisting of a base plate which is connected to elongated fixing elements in each case on both sides in the longitudinal direction of the bandage. A preferred S-shaped design is produced insofar as the ends of the fixing elements, which are secured to the base plate, are situated diagonally opposite one another. As a result, the pressure can be applied in an even more uniform manner and the bandage slipping out of the pressure applicator in an unwanted manner is better avoided. The W-shaped appearance is produced if the fixing elements are secured on the same side of the base plate.

The positioning of the bandage is produced almost intuitively for a user as a result of the design of the pressure applicator.

It is provided, in this case, that the bandage is initially applied to an injury by way of its wound dressing pad and then is unrolled and wrapped around a limb or another part of the body until the binding or bandage can be moved into engagement with the pressure applicator. The bandage is then inserted into the gap between the first fixing element and the base plate and there is then a directional change in the placing direction, as a result of which a first tightening is able to be applied and at the same time the first end is fixed. It is now also still possible, in this case, to adjust the position of the wound dressing pad with reference to the injury. The bandage is then wrapped around the relevant part of the body until the bandage comes into the region of the pressure applicator again and is inserted into the gap between the second fixing element and the base plate. If the bandage is then tightened, the desired pressure can thus be applied, the distribution of pressure being uniformly distributed on the injury by means of the pressure applicator as a result of the double change in direction of the bandage. The bandage can then be wrapped around the relevant position, as a result of which additional pressure is introduced perpendicularly into the injury by means of the pressure applicator. Said applied pressure is always produced when an additional element is wrapped under a corresponding binding. If the bandage is then attached to the carrier with reference to its full length, it can be secured by means of the fastening element, which is provided at the second end of the flat material web, for example on or to itself.

Various fastening elements are conceivable in this case. For example, a hook and loop element (Velcro fastening element) which can be secured to the bandage material, can thus be provided. Furthermore, a bow-shaped locking element is also conceivable, the free ends of the bow being able to be hooked under windings of the bandage. As an alternative to this, all further fastening elements known from the bandage and binding sector are possible. The term "fastening element" is also to be understood, in this case, as the second end of the bandage itself forming the fastening element by being inserted, for example, under other windings of the bandage and thus being secured via friction. Furthermore, this is also to be understood as when the fastening of the bandage on the carrier is effected by means of external elements, such as clips, etc., which interact with the second end which then forms the second fastening element. When a bow-shaped fastening element is provided, it can also be used for putting a tourniquet on the limb by the bow-shaped locking element being guided through under windings of the bandage located underneath it and being rotated about an axis perpendicularly to the binding plane and thus increasing the pressure on a wound. The bow-shaped locking element is then hooked by way of its end under windings located underneath it in a conventional manner and is fixed against derotation.

It is particularly preferred, in this case, when the base plate comprises a rectangular or parallelogram-like form. As a result, a comparatively extensive and uniform force introduction can be effected and in particular the fixing elements can be provided parallel to the longitudinal sides of the rectangle or parallelogram which can extend over a desired portion of the width of the bandage. Furthermore, the base plate can be realized in a flat manner or, as an alternative to this, can also be realized in a curved manner in order to provide anatomical adaption to a part of the body. Where applicable, it can also be designed in a flexible manner so that the base plate can be adapted to a certain extent to a part of the body.

In order to enable particularly simple application and in particular insertion of the bandage into the gap, it can be provided that the fixing elements extend beyond the base plate in particular transversely with respect to the longitudinal direction of the bandage. In this case, it is particularly desirable for reasons of the flat application of the tensile forces when the gaps extend perpendicularly, that is to say transversely with respect to the longitudinal direction of the bandage, as a particularly uniform tensile force can then be achieved and, at the same time, the bandage width is not constricted, that is to say the bandage width is not reduced, any more than necessary.

It is particularly preferred, in this case, when the gap between the fixing elements of the base plate extends in a substantially straight manner as this also has a positive influence on the progression of the bandage at the deflection. Insertion of the bandage between the fixing elements and the base plate becomes particularly simple when, as is provided in particular in a preferred manner, the fixing elements and/or the base plate are deformable elastically at least in portions. The gap, in this case, can comprise the same width over its length or can taper or widen. In addition, in order to prevent the bandage slipping out of the gap, it can be provided to arrange lugs at the free ends of the fixing elements which project into the gap, where applicable span said gap and consequently bear against the base plate.

The pressure applicator, in this case, is arranged preferably centrally above the wound dressing pad on the opposite side of the flat material web. As a result, the pressure can be applied in a particularly central manner and positioning of the wound dressing pad on an injury is possible in a particularly simple manner.

In order to improve simple positionability further and to facilitate the application, it can be provided that the flat material web comprises a holding portion at the first end. In this case, the first end is the end which is located on the outside in the case of a bandage which is configured in roll form and which is gripped first of all.

In order to achieve better manageability here, the holding portion can be formed as a result of the flat material web being folded over and secured on itself. Said holding portion which forms a double-layer end region and which can be fixed in particular by stitching, can comprise, for instance a length of between 5 and 15 cm, preferably of between 7 and 12 cm, and further preferably of approximately between 5 cm and 10 cm. Handling is particularly simplified as a result. The wound dressing pad preferably then follows on the inside of the bandage.

In this case, the wound dressing pad can preferably be designed in an absorbent manner and in particular can consist of a cladding material, the shell, on the side facing the wound or injury, being able to consist of a liquid-permeable, hydrophilic nonwoven material which is produced, in particular, from polypropylene or from a mixture of polyamide and viscose (55/45). A hydrophobic nonwoven material, preferably produced from polypropylene, can be provided on the side remote from the wound and consequently facing the bandage. The cladding layers can, however, also be realized in an identical manner. The two cladding layers can be connected together, for example, by ultrasound welding, but also by any arbitrary conventional connection method. The absorbent material, in this case, is preferably provided inside the shell. In this connection, this can be, for example, a core of cellulose fibers in a little compacted layer (fluff). In this case, further or additional materials can form the absorbent material or be provided therein, such as, for example, alginate, SAP, hemostatic or anti-infection materials.

Provided in a particularly preferred manner, in this case, can be when a further inner shell is provided which can be formed, for example, by a thin cellulose paper. The absorbent material, in particular the fluff material, can preferably be provided in the inner shell. This is then received in the outer cladding material.

It is particularly preferred, in this case, when the width of the wound dressing corresponds to the width of the bandage. Preferred bandage widths are 10 cm, 15 cm or 20 cm. Thus, it can be provided, for example, depending on the bandage width, to provide a wound dressing pad of 5×5 cm, but also of up to 20×40 cm. Particularly preferred, in this case, are wound dressing pads of 10×20 cm, 15×20 cm or 20×20 cm. Along with such rectangular wound dressing pads, square or round wound dressing pads are also conceivable. The wound dressing pads can be stitched or glued to the bandage or fastened to it in any other way. For example, the product Zetuvit® made by Paul Hartmann AG, Heidenheim, Germany is considered as a wound dressing pad.

The flat material web can preferably be a mono-elastic woven fabric; it is additionally particularly preferred, in this case, when the bandage is designed as a compression bandage. In this case, it is particularly preferred when the elasticity is achieved by using elastic warp threads. In the non-stretched state, such a bandage comprises a wavy surface. The elasticity of such bandages is achieved, as a rule, as a result of the elastic fibers, which are used as warp threads, being prestressed during the weaving process and then being destressed for packaging so that a wavy surface is realized. It is particularly preferred, in this case, when the bandage comprises an elasticity in the longitudinal direction of no more than 250%, in particular of no more than 200% and additionally of 160-200%, preferably of 175% or 200%.

The elasticity of the bandage is determinable in this case according to DIN 61632:2009-12.

The pressure applicator is preferably produced from plastics material and can consist in a particularly preferred manner of polycarbonate. Generally speaking, however, other plastics materials can also be used. In this case, the pressure applicator preferably comprises dimensions of between 50 and 80 mm, preferably of between 60 and 70 mm, in the longitudinal direction of the bandage. The extension transversely with respect to the longitudinal direction of the bandage is preferably between 5 and 15 mm smaller than the bandage width, preferably 10 mm smaller than the bandage width.

It is particularly preferred in this case when the compression bandage is packaged in roll form so that the first end of the flat material web is located on the outside.

In this case, it is additionally particularly preferred when it is possible to unroll a first region with one hand and further unrolling is then initially prevented by an unroll lock. Said first region can be preferably less than 60 cm, preferably less than 50 cm and preferably between 35 cm and 45 cm. As a result, handling of the bandage is improved as the person positioning the bandage is able to concentrate on the wound dressing pad in said first phase and does not have to be careful to hold the bandage securely and not allow it to unwind in an unwanted manner.

It can be provided additionally, as is disclosed in the prior art, also to provide an adhering element either mechanically or adhesively or cohesively in the region of the first end in order to secure the first winding.

In principle, however, the securing of the first winding on itself just as a result of the friction of the layers on one another is also to be seen as sufficient.

To continue positioning the bandage—if an unroll lock is provided—it is then necessary for the unroll lock to be removed. It can be provided to this end that the unroll lock is releasable and/or destructible. For example, it can be provided that a thread is provided as an unroll lock, which thread connects the uppermost layer of the bandage roll to layers located underneath it and thus prevents further unrolling from the position of the bandage provided with the unroll lock. The thread can then be destroyed as a result of a stronger tug so that the bandage is able to unroll fully and consequently can be positioned on a patient.

The bandage is then positioned, in this case, as follows: To apply the bandage, it is removed from a packaging, it preferably being provided that the bandage can be packaged in a sterile manner. The first end of the bandage is held with the hand and the bandage is then able to unroll automatically as a result of releasing the roll-shaped body until it reaches the unroll lock, the unroll lock preventing further unrolling. The wound dressing pad is exposed in this way and can be placed on a wound or injury to be covered. It is not necessary to hold and secure the rest of the bandage which is still present in roll form at the same time so that both hands are available in said first phase of wound treatment. The bandage is wound around the area of the body on which the wound is located. The pressure applicator, which is arranged on the opposite side of the bandage, is also exposed simultaneously with the wound dressing pad. In the positioned state, the wound applicator, in this case, points outward. The bandage is then wound around the area of the body until the region of the pressure applicator is reached. It is then hooked into the pressure applicator by the bandage being inserted into the gap between the first fixing element and the base plate. The winding direction of the bandage is then changed. Insertion is effected, in this case, from the bandage-facing side of the fixing element. That is, the bandage runs through under the fixing element, through the gap and, changing direction, beyond said gap. In this case, the first fixing element is to be understood as the fixing element which is reached first by the bandage when it is wrapped around the part of the body. Once the winding direction has been changed, the bandage is then wound a further time around the relevant part of the body until the pressure applicator is reached again, now in the region of the second fixing element, and the bandage is hooked into the pressure applicator, once again by being inserted into the gap between the second fixing element and the base plate. This is effected as described above. The required pressure is exerted on the wound by the pressure applicator as a result of tightening the bandage. The pressure, in this case, is applied to the wound substantially by the base plate. If the wound dressing slips out of place when the bandage is put on, it is now still possible to correct the position. Such a positional correction can be necessary if, for example, too much tension is applied after hooking-in the bandage on the first side of the pressure applicator and the bandage is entrained on the part of the body. Finally, the bandage is then wound further around the relevant part of the body until the end is reached. The positioned bandage is fixed by means of the fastening element, in particular an end locking clip.

Figure 2:
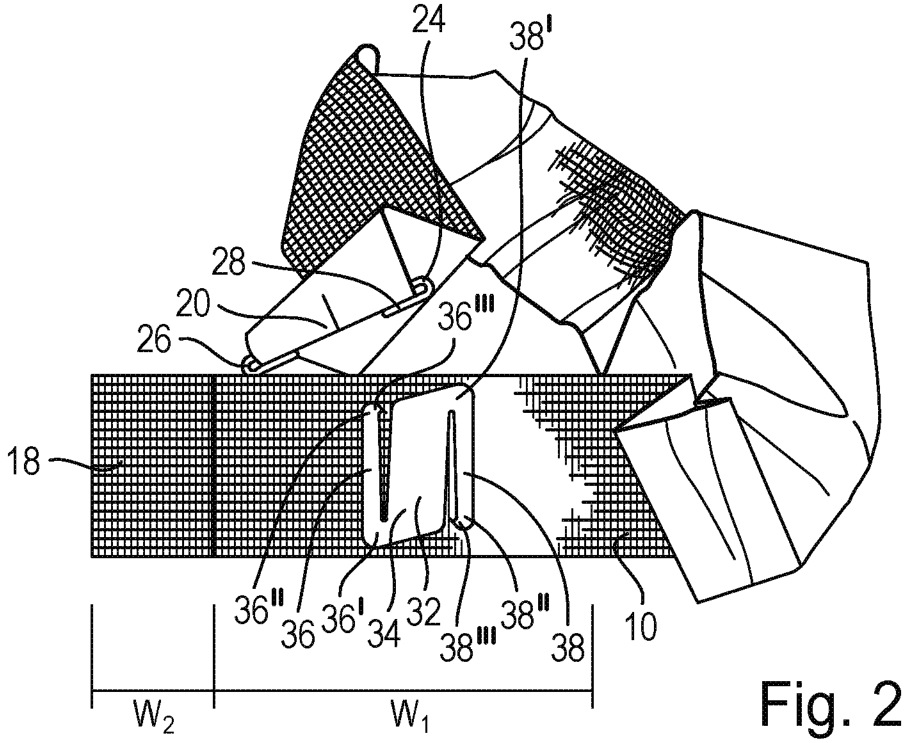

The invention is to be explained in more detail below by way of a drawing, in which:

FIG. 1 shows a first perspective view of the bandage according to the invention, FIG. 2 shows a further view of the bandage according to the invention.

FIG. 1 shows a bandage 10 according to the invention, the roll form in which the bandage is packaged still being visible at the right-hand edge of the image. In this case, the bandage has been unrolled up to an unroll lock 30. The length of the already unrolled end is approximately 40 cm. The bandage comprises a flat material web which is characterized by way of the reference symbol 12, having a first side 14 and a second side 16. Furthermore, the flat material web has two ends 18 and 20, the second end 20 in FIG. 1 being situated inside the configuration that is still rolled up. The bandage 10 of the exemplary embodiment is mono-elastic, the wavy form of the flat material web being visible in the relaxed state both in FIG. 1 and in FIG. 2 which is produced as a result of the elastic warp threads being stretched during the weaving process and then relaxing. The extensibility is approximately 200%. On the first side 14 of the bandage 10 there is a wound dressing pad 22 where an absorbent material is provided in an inner shell and said inner shell is surrounded by two nonwoven layers as cladding layers of a shell, the nonwoven layers being designed such that it is possible for liquid to enter the wound dressing pad from a wound. In addition, it can be provided that the wound-remote side of the wound dressing pad 22 is realized in a liquid-impermeable manner or at least in a liquid-repellent manner.

The wound dressing pad 22, in this case, preferably extends over the entire width of the bandage 10. The wound dressing pad 22 can be fixed to the bandage 10 in an adhesive manner or by means of stitching. The length of the wound dressing pad is characterized in FIG. 2 by way of the reference symbol $W_1$.

A type of holding portion is designed at the first end 18 of the bandage as a result of part of the bandage being folded over on itself and being stitched there. Said holding portion has a length $W_2$ which is approximately 7 cm. As a result, the first end 18 is stabilized and can be better handled. The wound dressing pad has an extension of approximately 10×20 cm and the bandage comprises a width of approximately 10 cm. Provided at the second end 20 is a fastening element 24, which is formed here by a safety clip 26 which, when the bandage 10 has been completed on a patient, can be hooked under windings that are located further underneath it by way of its two clip elements 28. In order to achieve a tourniquet effect, the pressure on a wound can be further increased in a known manner by means of the safety clip by rotating the same about an axis perpendicular to the bandage plane.

In order to prevent the bandage unrolling more than is desired whilst the wound dressing pad 22 is placed on a wound, an unroll lock 30 is provided which is formed by a thread which connects one of the bandage windings to a winding located underneath it and thus prevents further unrolling. If the first fixing of the wound dressing is successful and if the entire bandage is to be fixed to the person, the unroll lock can be released or in the present case can be destroyed by tearing the thread. The unroll lock 30, in this case, is preferably attached in such a manner that the wound dressing pad 22 can be placed on a wound and the bandage 10 can then be wrapped once around the part of the body to be treated so that the bandage 10 can then be fixed in a pressure applicator 32. The fixing is effected, in this case, by the pressure applicator 32 consisting of a base plate 34, by way of which the pressure applicator 32 is fixed to the bandage 10, and two fixing elements 36 and 38 which are provided on both sides of the base plate 34 in the longitudinal direction. In the present exemplary embodiment, the base plate 34, in this case, comprises a parallelogram-like form and consists, just as the fixing elements 38, 38 which are integrally connected thereto, of a polycarbonate. The fixing elements 36, 38 enclose a gap between them and the base plate 34, the gap being able to be realized either substantially the same over the entire length or, as in the present case here, being able to widen in a V-shaped manner. The fixing elements 36, 38 are integrally connected by way of an end 36' or 38' to the base plate 34, the ends 36' and 38' being located substantially diagonally opposite one another. The other ends 36" and 38" are free so that the bandage is able to be inserted into the gap between the base plate 34 and the fixing elements 36, 38.

In order to prevent unwanted release of the bandage from the gap, lugs 36" or 38'", which secure the bandage 10 in the gap, are provided at the free ends 36", 38".

When being positioned, the bandage 10 is then initially unrolled up to the unroll lock 30 and the wound dressing pad 22 is placed on the injury. The bandage 10 is then placed around the relevant part of the body and pushed into the first gap between the first fixing element 36 and the base plate 34. As a result, a first fixing is reached. The winding direction is then changed and, by destroying the thread which forms the unroll lock, the bandage 10 is once again wrapped around the relevant part of the body up to the second fixing element 38 and there is inserted into the gap between fixing element 38 and base plate 34. As a result of tensioning the bandage, pressure can then be exerted onto the wound by means of the base plate 34, said pressure being achieved as a result of corresponding tightening. Reversing the winding direction twice, which is changed again after hooking-in behind the fixing element 38, results in the pressure being applied in a very uniform manner. The bandage 10 is then fully wound firmly on the relevant person and the bandage 10 is fixed at the end by means of the fastening element 26.

In the afore-described manner, force is able to be introduced uniformly and a bandage applied in a particularly simple manner even in emergency situations.

The invention claimed is:

1. A bandage (10) including a. a flat material web (12) having a first (14) and a second (16) side and a first (18) and second (20) end which are spaced apart in a longitudinal direction of the bandage (10) with respect to a longitudinal axis of the bandage (10), the flat material web (12) having first and second edges extending between the first end (18) and the second end (20) which are spaced in a lateral direction of the bandage (10) with respect to a lateral axis of the bandage (10), the lateral axis being orthogonal to the longitudinal axis, b. a wound dressing pad (22) on the first side of the flat material web (12), the wound dressing pad (22) extending across a portion of the first side and being positioned entirely between the first edge and the second edge, c. a pressure applicator (32) secured to the second side (16) of the flat material web (12) opposite the wound dressing pad (22), d. a fastening element (24) at the second end (20) of the flat material web (12) for fastening the second end (20) of the flat material web (12) on or to itself when the bandage (10) is positioned on a carrier, wherein the pressure applicator (32) comprises a one-piece base plate (34) and two elongated fixing elements (36, 38) in a substantially S-shape or Z-shape, wherein each of the two elongated fixing elements (36, 38) have two ends (36', 36", 38', 38") located towards opposing ends of the width of the bandage (10) such that the two elongated fixing elements (36, 38) are arranged in the longitudinal direction of the bandage (10) on both sides of the one-piece base plate (34) and extend at an angle to the longitudinal direction of the bandage (10), in each case only one first end (36', 38') of each of the elongated fixing elements (36, 38) is integrally secured to the one-piece base plate (34) and only the other second end (36", 38") of the same respective elongated fixing element is free, the elongated fixing elements (36, 38) define a gap between them and the one-piece base plate (34) over their respective remaining lengths such that the second ends (36", 38") are spaced from the base plate (34) to enable reception of at least the flat material web (12) through respective sides of the pressure applicator (32), the first ends (36', 38') of the fixing elements (36, 38) secured to the one-piece base plate (34) are situated diagonally opposite one another, wherein the one-piece base plate (34) defines a maximum lateral dimension extending in the lateral direction of the bandage, the maximum lateral dimension of the base plate (34) being greater than 50% but less than 97.5% of the total width of the bandage (10); and wherein the pressure applicator (32) is configured to apply uniform pressure in a direction towards a wound in a centralized manner via at least the base plate (34) when placed on top of the wound.

2. The bandage (10) as claimed in claim 1, wherein the one-piece main body (34) defines a longitudinal dimension extending in the longitudinal direction and wherein each of the two elongated fixing elements (36, 38) define a corresponding longitudinal dimension extending in the longitudinal direction and wherein the longitudinal dimension of the base plate (34) is greater than the longitudinal dimension of each of the two elongated fixing elements (36, 38).

3. The bandage (10) as claimed in claim 2, wherein each of the two elongated fixing elements (36, 38) is configured such that the gaps defined between the two elongated fixing elements (36, 38) and the one-piece main body (34) increase or widen in the longitudinal direction toward the second ends (36", 38") of the two elongated fixing elements (36, 38).

4. The bandage (10) as claimed in claim 3, wherein the gaps each define a V-shape.

5. The bandage (10) as claimed in claim 1, wherein a holding portion is realized at the first end (18) of the flat material web (12).

6. The bandage (10) as claimed in claim 5, wherein the wound dressing pad (22) connects to the holding portion in the longitudinal direction of the bandage.

7. The bandage (10) as claimed in claim 1, wherein the bandage (10) is packaged in a roll form so that the first end (18) of the flat material web (12) is on the outside.

8. The bandage (10) as claimed in claim 7, wherein a releasable and/or destructible unroll lock is provided which prevents further unrolling after a defined length proceeding from the first end (18).

9. The bandage (10) as claimed in claim 1, wherein both said fixing elements (36, 38) are configured to only receive the second end (20) of the flat material web (12).

10. The bandage (10) as claimed in claim 9, wherein said fixing elements (36, 38) are configured to each receive a 180° reverse turn of the second end (20) of the flat material web (12) without passing over the one-piece base plate (34), followed by concentrically wrapping the second end (20) of the flat material web (12) about both the one-piece base plate (34) and fixing elements (36, 38) to secure the bandage (10) on top of the wound.

11. The bandage (10) as claimed in claim 1, wherein the one-piece base plate (34) comprises a parallelogram-like form and wherein the sides of the base plate (34) defining the gaps are straight or linear.

12. The bandage (10) as claimed in claim 1, wherein the second free ends (36", 38") of the fixing elements (36, 38) project beyond the one-piece base plate (34) with respect to the longitudinal direction of the bandage (10).

13. The bandage (10) as claimed in claim 1, wherein the pressure applicator (32) is arranged centrally above the wound dressing pad (22).

14. The bandage (10) as claimed in claim 1, wherein the fixing elements (36, 38) and/or the one-piece base plate (34) are deformable elastically at least in portions.

15. The bandage (10) as claimed in claim 1, wherein the flat material web (12) consists of a mono-elastic woven fabric.

16. The bandage (10) as claimed in claim 1, wherein the bandage (10) is a compression bandage.

17. The bandage (10) as claimed in claim 1, wherein the wound dressing pad comprises a shell which is filled with an absorbent material.

18. The bandage (10) as claimed in claim 1, wherein the gap is configured to receive several turns of a single free end (20) of the flat material web (12).

19. The bandage (10) as claimed in claim 1, additionally comprising lugs (36", 38") provided at the free ends (36", 38") of the fixing elements (36, 38).

20. The bandage (10) as claimed in claim 1, wherein the base plate (34) of the pressure applicator (32) is secured to the bandage (10).

21. A bandage (10) including;

a. a flat material web (12) having a first (14) and a second (16) side and a first (18) and second (20) end which are spaced apart in the longitudinal direction of the bandage (10) with respect to a longitudinal axis of the bandage (10), the flat material web (12) having first and second edges extending between the first end (18) and the second end (20) which are spaced in a lateral direction of the bandage (10) with respect to a lateral axis of the bandage (10), the lateral axis being orthogonal to the longitudinal axis, b. a wound dressing pad (22) disposed on a portion of the first side (14) of the flat material web (12), the wound dressing pad (22) being positioned entirely between the first edge and the second edge and entirely at a position between the first end (18) and the second end (20) of the flat material web (12), c. a pressure applicator (32) secured to the second side (16) of the flat material web (12) opposite the wound dressing pad (22), d. a fastening element (24) at the second end (20) of the flat material web (12) for fastening the second end (20) of the flat material web (12) on or to itself when the bandage (10) is positioned on a carrier, the fastening element (24) including a clip (26) having two clip elements (28) configured to hook onto a winding of the flat web material (12), wherein:

the pressure applicator (32) comprises a one-piece base plate (34) and two elongated fixing elements (36, 38) in a substantially S-shape or Z-shape, each of the two elongated fixing elements (36, 38) have two ends (36', 36": 38', 38") located towards opposing ends of the width of the bandage (10) such that two elongated fixing elements (36, 38) are arranged in the longitudinal direction of the bandage (10) on both sides of the one-piece base plate (34) and extend at an angle to the longitudinal direction of the bandage (10), in each case only one first end (36', 38') of each of the elongated fixing elements (36, 38) is integrally secured to the one-piece base plate (34) and only the other second end (36", 38") of the elongated fixing elements of the same respective elongated fixing element is free, the elongated fixing elements (36, 38) define a gap between them and the one-piece base plate (34) over their respective remaining lengths such that the second ends (36", 38") are spaced from the one-piece base plate (34) to enable reception of at least the flat material web (12) through respective sides of the pressure applicator (32), the first ends (36', 38') of each of the fixing elements (36, 38) secured to the one-piece base plate (34) are situated diagonally opposite one another, the one-piece base plate (34) comprises a parallelogram-like form, wherein the one-piece base plate (34) defines a maximum lateral dimension extending in the lateral direction of the bandage, the maximum lateral dimension of the base plate (34) being greater than 50% but less than 97.5% of the total width of the bandage (10), and wherein the pressure applicator (32) is configured to apply uniform pressure in a direction towards a wound in a centralized manner when placed on top of the wound.

22. The bandage (10) as claimed in claim 21, wherein each of the two elongated fixing elements (36, 38) is configured such that the gaps defined between the two elongated fixing elements (36, 38) and the one-piece main body (34) increase or widen in the longitudinal direction toward the second ends (36", 38") of the two elongated fixing elements (36, 38).

23. The bandage (10) as claimed in claim 22, wherein the gaps each define a V-shape.

24. The bandage (10) as claimed in claim 21, wherein the one-piece main body (34) defines a longitudinal dimension extending in the longitudinal direction and wherein each of the two elongated fixing elements (36, 38) define a corresponding longitudinal dimension extending in the longitudinal direction and wherein the longitudinal dimension of the base plate (34) is greater than the longitudinal dimension of each of the two elongated fixing elements (36, 38).

25. A bandage (10) including a flat material web (12) having a first (14) and a second (16) side and a first end (18) and second end (20) which are spaced apart in a longitudinal direction of the bandage (10) with respect to a longitudinal axis of the bandage (10), the flat material web (12) having first and second edges extending between the first end (18) and the second end (20) which are spaced in a lateral direction of the bandage (10) with respect to a lateral axis of the bandage (10), the lateral axis being orthogonal to the longitudinal axis, a wound dressing pad (22) on the first side of the flat material web (12), the wound dressing pad (22) extending across a portion of the first side, a pressure applicator (32) secured to the second side (16) of the flat material web (12) opposite the wound dressing pad (22), the pressure applicator (32) comprises a base plate (34) and two elongated fixing elements (36, 38) extending from the base plate, wherein each of the two elongated fixing elements (36, 38) have two ends (36', 36", 38', 38") located towards opposing ends of the width of the bandage (10) such that the two elongated fixing elements (36, 38) are arranged in the longitudinal direction of the bandage (10) on both sides of the base plate (34) and extend at an angle to the longitudinal direction of the bandage (10), wherein the elongated fixing elements (36, 38) are configured to define a gap between each of the elongated fixing elements (36, 38) and the base plate (34) over the respective remaining lengths of the elongated fixing elements (36, 38) such that the second ends (36", 38") are spaced from the base plate (34) in non-contacting relation therewith, wherein the base plate (34) defines a longitudinal dimension extending in the longitudinal direction and wherein each of the two elongated fixing elements (36, 38) define a corresponding longitudinal dimension extending in the longitudinal direction and wherein the longitudinal dimension of the base plate (34) is greater than the longitudinal dimension of each of the two elongated fixing elements (36, 38), wherein the base plate (34) defines a maximum lateral dimension extending in the lateral direction of the bandage, the maximum lateral dimension of the base plate (34) being greater than 50% but less than 97.5% of the total width of the bandage (10), and wherein the pressure applicator (32) is configured to apply uniform pressure in a direction towards a wound in centralized manner when placed on top of the wound.

26. The bandage (10) as claimed in claim 25, wherein the base plate (34) comprises a parallelogram-like form such that the sides of the base plate (34) defining the gaps are straight or linear.

* * * * *